(12) United States Patent
Goodman et al.

(10) Patent No.: US 7,817,050 B2
(45) Date of Patent: Oct. 19, 2010

(54) ULTRASONIC GAS LEAK DETECTOR WITH AN ELECTRICAL POWER LOSS AND CARBON FOOTPRINT OUTPUT

(75) Inventors: Mark A. Goodman, Cortlandt, NY (US); Gary Mohr, Cortlandt Manor, NY (US); William Bishop, Pleasantville, NY (US)

(73) Assignee: U.E. Systems Inc., Elmsford, NY (US)

( * ) Notice: Subject to any disclaimer, the term of this patent is extended or adjusted under 35 U.S.C. 154(b) by 316 days.

(21) Appl. No.: 12/228,087

(22) Filed: Jun. 4, 2008

(65) Prior Publication Data

US 2009/0303058 A1    Dec. 10, 2009

Related U.S. Application Data (63) Continuation-in-part of application No. 11/339,811, filed on Jan. 24, 2006, now abandoned, which is a continuation-in-part of application No. 10/386,008, filed on Mar. 11, 2003, now Pat. No. 6,996,030, which is a continuation-in-part of application No. 10/292,799, filed on Nov. 12, 2002, now Pat. No. 6,707,762.

(51) Int. Cl.
  *G08B 17/10*   (2006.01)
  *G01M 3/04*   (2006.01)
  *G05D 3/12*   (2006.01)
  *G05D 3/00*   (2006.01)
  *G05D 9/00*   (2006.01)
  *G05D 11/00*   (2006.01)
  *G05D 17/00*   (2006.01)

(52) U.S. Cl. .............. 340/632; 73/40; 700/291

(58) Field of Classification Search ........... 340/605, 340/632; 73/40; 700/291, 301, 286
See application file for complete search history.

(56) References Cited

U.S. PATENT DOCUMENTS 3,374,663 A    3/1968  Morris (Continued)

FOREIGN PATENT DOCUMENTS

JP    11142279 A    5/1999
JP    2007333550 A    12/2007

OTHER PUBLICATIONS

Simon Gandy, A guide to the range and suitability of electrical energy storage systems for various applications, and an assessment of possible policy effects; Sep. 2000; Imperial College of Science, Technology and Medicine (University of London) Centre for Environmental Technology T H Huxley School of Environment, Earth Sciences and Engineering.*

(Continued)

*Primary Examiner*—Jennifer Mehmood
(74) *Attorney, Agent, or Firm*—Leason Ellis LLP (57) ABSTRACT

A system determines the carbon footprint of a compressed gas leak. The system comprises an ultrasonic detector to detect a compressed gas leak, a storage device storing information on the type of gas, the compressor efficiency, and the carbon emissions necessary to generate electricity to drive the compressor. A processing unit includes software that determines an amount of electrical energy needed to recharge the lost compressed gas based on the compressor efficiency and calculates the carbon emissions created by the amount of electrical energy. A method monitoring for gas leaks comprises detecting ultrasonic emissions, generating an electrical signal representative of the compressed gas leak, and calculating an amount of electrical energy needed to recharge the lost compressed gas. The method further includes calculating the carbon footprint based on the carbon emissions necessary for the electrical power generation system that drives the compressor.

26 Claims, 11 Drawing Sheets

U.S. PATENT DOCUMENTS

| | | | |
|---|---|---|---|
| 3,964,014 A | 6/1976 | Tehon | |
| 3,978,915 A | 9/1976 | Harris | |
| 4,027,242 A | 5/1977 | Yamanaka | |
| 4,034,332 A | 7/1977 | Alais | |
| 4,095,173 A | 6/1978 | Darrel | |
| 4,287,581 A * | 9/1981 | Neale, Sr. | 367/135 |
| 4,353,245 A * | 10/1982 | Nicolai | 73/49.2 |
| 4,420,707 A | 12/1983 | VanValkenburg | |
| 4,439,723 A | 3/1984 | Loftness | |
| 4,629,834 A | 12/1986 | Waggoner et al. | |
| 4,785,659 A | 11/1988 | Rose et al. | |
| 4,823,600 A * | 4/1989 | Biegel et al. | 73/592 |
| 4,987,769 A * | 1/1991 | Peacock et al. | 73/49.7 |
| 5,025,666 A | 6/1991 | Kobayashi et al. | |
| 5,075,629 A | 12/1991 | Umemura et al. | |
| 5,089,997 A | 2/1992 | Pecukonis | |
| 5,103,675 A | 4/1992 | Komninos | |
| RE33,977 E | 6/1992 | Goodman et al. | |
| 5,136,876 A | 8/1992 | Taylor | |
| 5,267,221 A | 11/1993 | Miller et al. | |
| 5,432,755 A | 7/1995 | Komninos | |
| 5,530,366 A | 6/1996 | Nasrallah | |
| 5,535,136 A | 7/1996 | Standifer | |
| 5,719,785 A * | 2/1998 | Standifer | 702/51 |
| 6,247,353 B1 | 6/2001 | Battenberg et al. | |
| 6,377,184 B1 | 4/2002 | Minker | |
| 6,701,298 B1 | 3/2004 | Jutsen | |
| 6,707,762 B1 * | 3/2004 | Goodman et al. | 367/135 |
| 6,804,992 B2 | 10/2004 | Goodman et al. | |
| 6,850,848 B2 | 2/2005 | Nguyen et al. | |
| 7,081,757 B2 | 7/2006 | Unsworth et al. | |
| 7,130,804 B2 | 10/2006 | Fujiwara | |
| 7,298,278 B2 * | 11/2007 | Miller et al. | 340/603 |
| 7,343,341 B2 | 3/2008 | Sandor et al. | |
| 7,423,541 B2 * | 9/2008 | Miller | 340/612 |
| 2003/0083980 A1 | 5/2003 | Satake | |
| 2004/0039684 A1 | 2/2004 | Sandor | |
| 2004/0230443 A1 | 11/2004 | McMorris et al. | |
| 2005/0145018 A1 | 7/2005 | Sabata et al. | |
| 2006/0020502 A1 | 1/2006 | Trout et al. | |
| 2006/0184445 A1 | 8/2006 | Sandor et al. | |
| 2007/0057802 A1 | 3/2007 | Fujiwara | |
| 2007/0203722 A1 | 8/2007 | Richards et al. | |
| 2007/0233502 A1 | 10/2007 | Richards et al. | |
| 2007/0250329 A1 | 10/2007 | Richards et al. | |

OTHER PUBLICATIONS

"Industrial Compressed Air Ultrasonic Leak Detection Survey Guide," SDT North America 2003, available at http://www.beizein.nl/Downloads/Leak_Survey_Handbook.pdf, last visited on Jan. 8, 2010.

2009 Compressed Air Leak Surveyor Handbook, 3rd. edition, available at http://www.sdtnorthamerica.com/PDFs/Leak_Survey_Handbook.pdf, Last visited on Jan. 8, 2010.

Industrial Compressed Air Ultrasonic Leak Detection Survey Guide, undated, available at http://www.sdtnorthamerica.com/PDFs/Leak_Survey_Handbook.pdf, visited Jul. 14, 2008.

* cited by examiner

This is for year 2008

| Cost Calculations | |
|---|---|
| State = | New York |
| Electricity Cost = | $ 0.10 Per kWh |
| Air Cost = | $ 0.33 Per 1000 Cubic Feet |
| Argon Cost = | $ 22.80 Per 1000 Cubic Feet |
| Helium Cost = | $ 99.95 Per 1000 Cubic Feet |
| Hydrogen Cost = | $ 11.77 Per 1000 Cubic Feet |
| Nitrogen Cost = | $ 3.80 Per 1000 Cubic Feet |

| Operational Times | |
|---|---|
| Hours Per Day | 24 |
| Days Per Year | 365 |

FIG. 7

| $351.80 | | | Air Leaks Repaired | | Argon Leaks Repaired | | Helium Leaks Repaired | | Hydrogen Leaks Repaired | | Nitrogen Leaks Repaired | | Carbon Dioxide CO2(lbs) | | Nitrogen Oxide NO (lbs) | | Sulfur Dioxide SO2 (lbs) | | |
|---|---|---|---|---|---|---|---|---|---|---|---|---|---|---|---|---|---|---|---|
| | Repaired Leaks Cost Avoidance | % Complete | CFM | Cost | CFM | Cost | CFM | Cost | CFM | Cost | CFM | Cost | Identified Avoidance | Realized Avoidance | Identified Avoidance | Realized Avoidance | Identified Avoidance | Realized Avoidance | Focus Area |
| Identified Leaks Cost Avoidance | | | | | | | | | | | | | | | | | | | |
| $351.80 | | | | | | | | | | | | | 2778 | | 3 | | 7 | | |

Notes:

| December 2008 | | | | | | | | | | | | | | | | | | | | | | |
|---|---|---|---|---|---|---|---|---|---|---|---|---|---|---|---|---|---|---|---|---|---|---|
| | | | Air Leaks Repaired | | Argon Leaks Repaired | | Helium Leaks Repaired | | Hydrogen Leaks Repaired | | Nitrogen Leaks Repaired | | | | | Cost Avoidance | | | | | | |
| | | | CFM | Cost | CFM | Cost | CFM | Cost | CFM | Cost | CFM | Cost | | | | Identified | Repaired | % complete | | | | |
| | | | 0.0 | $0.00 | 0.0 | $0.00 | 0.0 | $0.00 | 0.0 | $0.00 | 0.0 | $0.00 | | | | $0.00 | $0.00 | 0 | | | | |
| Record Number | Group Name | Location Name | Type of Gas | Pressure at Leak | dB Reading | Problem Description | | | | | Repaired (Y/N) | Work Schedule # | Identified Leaks Cost Avoidance | Size of Leak CFM | Energy Avoidance (kWh) | CO2 Avoidance (lbs) | NO Avoidance (lbs) | SO2 Avoidance (lbs) |
| 1 | May air leaks | Floor 1 | Air | 100 | 23 | | | | | | | | $105.72 | 1.1 | 1057 | 1057 | 835 | 5 |
| 2 | May air leaks | Floor 1 | Air | 100 | 44 | | | | | | | | $262.24 | 2.8 | 2622 | 2071 | 3 | 5 |
| 3 | May air leaks | Floor 1 | Air | 100 | 19 | | | | | | | | $80.90 | 0.9 | 809 | 639 | 1 | 2 |
| 4 | May air leaks | Floor 1 | Air | 100 | 25 | | | | | | | | $118.82 | 1.3 | 1188 | 938 | 2 | 2 |
| 5 | May air leaks | Floor 1 | Air | 100 | 10 | | | | | | | | $32.93 | 0.4 | 329 | 260 | 0 | 1 |
| 6 | May air leaks | Floor 1 | Air | 100 | 28 | | | | | | | | $139.25 | 1.5 | 1393 | 1100 | 1 | 3 |
| 7 | May air leaks | Floor 1 | Air | 100 | 17 | | | | | | | | $69.23 | 0.7 | 692 | 547 | 1 | 1 |
| 8 | May air leaks | Floor 1 | Air | 100 | 9 | | | | | | | | $28.41 | 0.3 | 284 | 224 | 0 | 1 |
| 9 | May air leaks | Floor 1 | Air | 100 | 12 | | | | | | | | $42.51 | 0.5 | 425 | 336 | 0 | 1 |
| 10 | May air leaks | Floor 1 | Air | 100 | 34 | | | | | | | | $182.76 | 2.0 | 1828 | 1443 | 2 | 3 |
| 11 | May air leaks | | Air | 100 | 23 | | | | | | | | $105.72 | 1.1 | 1057 | 835 | 1 | 2 |

| FLOW RATE CHART – CFM | | | | | | | | | | | | | Air | |
|---|---|---|---|---|---|---|---|---|---|---|---|---|---|---|
| Sensitivity | 150 PSI | | 125 PSI | | 100 PSI | | 75 PSI | | 50 PSI | | 25 PSI | | 10 PSI | |
| dB Reading | Leak Rate | Cost | Leak Rate | Cost | Leak Rate | Cost | Leak Rate | Cost | Leak Rate | Cost | Leak Rate | Cost | Leak Rate | Cost |
| 1.00 | 0.03 | $ 5.14 | 0.02 | $ 3.46 | 0.01 | $ 2.42 | 0.01 | $ 1.42 | 0.00 | $ 0.54 | 0.00 | $ 0.17 | 0.00 | $ 0.07 |
| 2.00 | 0.07 | $ 12.40 | 0.05 | $ 8.75 | 0.04 | $ 6.39 | 0.02 | $ 4.00 | 0.01 | $ 1.73 | 0.00 | $ 0.65 | 0.00 | $ 0.29 |
| 3.00 | 0.12 | $ 20.76 | 0.09 | $ 15.07 | 0.07 | $ 11.28 | 0.04 | $ 7.35 | 0.02 | $ 3.42 | 0.01 | $ 1.42 | 0.00 | $ 0.68 |
| 4.00 | 0.17 | $ 29.92 | 0.13 | $ 22.16 | 0.10 | $ 16.87 | 0.07 | $ 11.31 | 0.03 | $ 5.55 | 0.01 | $ 2.47 | 0.01 | $ 1.23 |
| 5.00 | 0.23 | $ 39.73 | 0.17 | $ 29.88 | 0.13 | $ 23.06 | 0.09 | $ 15.80 | 0.05 | $ 8.09 | 0.02 | $ 3.79 | 0.01 | $ 1.96 |
| 6.00 | 0.29 | $ 50.09 | 0.22 | $ 38.15 | 0.17 | $ 29.76 | 0.12 | $ 20.76 | 0.06 | $ 11.00 | 0.03 | $ 5.38 | 0.02 | $ 2.86 |
| 7.00 | 0.35 | $ 60.94 | 0.27 | $ 46.91 | 0.21 | $ 36.94 | 0.15 | $ 26.15 | 0.08 | $ 14.27 | 0.04 | $ 7.23 | 0.02 | $ 3.93 |
| 8.00 | 0.42 | $ 72.21 | 0.32 | $ 56.10 | 0.26 | $ 44.53 | 0.18 | $ 31.94 | 0.10 | $ 17.88 | 0.05 | $ 9.34 | 0.03 | $ 5.19 |
| 9.00 | 0.49 | $ 83.88 | 0.38 | $ 65.69 | 0.30 | $ 52.52 | 0.22 | $ 38.10 | 0.13 | $ 21.80 | 0.07 | $ 11.71 | 0.04 | $ 6.63 |
| 10 | 0.55 | $ 95.90 | 0.44 | $ 75.65 | 0.35 | $ 60.87 | 0.26 | $ 44.61 | 0.15 | $ 26.04 | 0.08 | $ 14.33 | 0.05 | $ 8.25 |

| FLOW RATE CHART – CFM | | | | | | | | | | | | | |
|---|---|---|---|---|---|---|---|---|---|---|---|---|---|
| | 150 PSI | | 125 PSI | | 100 PSI | | 75 PSI | | Air 50 PSI | | 25 PSI | | 10 PSI |
| dB | Leak Rate | Cost | Leak Rate | Cost | Leak Rate | Cost | Leak Rate | Cost | Leak Rate | Cost | Leak Rate | Cost | Leak Rate | Cost |
| 118 | 12.78 | $2,209.96 | 11.94 | $2,065.36 | 11.16 | $1,929.49 | 10.40 | $1,798.58 | 9.67 | $1,672.79 | 9.44 | $1,632.14 | 8.03 | $1,387.97 |
| 119 | 12.92 | $2,233.79 | 12.08 | $2,088.85 | 11.29 | $1,952.43 | 10.53 | $1,821.46 | 9.81 | $1,696.77 | 9.59 | $1,658.78 | 8.17 | $1,412.51 |
| 120 | 13.06 | $2,257.68 | 12.22 | $2,112.40 | 11.42 | $1,975.44 | 10.67 | $1,844.43 | 9.95 | $1,720.89 | 9.75 | $1,685.62 | 8.31 | $1,437.27 |

Note: dB row header has 8 sub-column pairs (Leak Rate / Cost) — the table shows 7 pressure groupings as above.

| Orifice Leak Rate | | | | | | Based on 8760 Hours/Year | | | | | | | |
|---|---|---|---|---|---|---|---|---|---|---|---|---|---|
| | 150 PSI | | 125 PSI | | 100 PSI | | Reference only 75 PSI | | Air 50 PSI | | 25 PSI | | |
| Diameter of Leak | Leak Rate | | | | | | | | | | | | |
| 1/64" | 0.58 | $ 100.6 | 0.49 | $ 85.42 | 0.41 | $ 70.21 | 0.32 | $ 54.99 | 0.23 | $ 39.60 | 0.14 | $ 24.21 | |
| 1/32" | 2.37 | $ 409.83 | 1.98 | $ 342.39 | 1.62 | $ 280.13 | 1.27 | $ 219.61 | 0.92 | $ 158.40 | 0.56 | $ 96.84 | |
| 1/16" | 9.45 | $ 1,634.12 | 7.9 | $ 1,366.09 | 6.49 | $ 1,122.27 | 5.08 | $ 878.45 | 3.66 | $ 632.90 | 2.25 | $ 389.08 | |
| 1/8" | 37.5 | $ 6,484.59 | 31.6 | $ 5,464.35 | 26 | $ 4,495.98 | 20.3 | $ 3,510.32 | 14.7 | $ 2,541.96 | 8.98 | $ 1,552.84 | |
| 1/4" | 150 | $ 25,938.36 | 126 | $ 21,788.22 | 104 | $ 17,983.93 | 81.3 | $ 14,058.59 | 58.6 | $ 10,133.25 | 35.9 | $ 6,207.91 | |
| 3/8" | 338 | $ 58,447.77 | 284 | $ 49,109.96 | 234 | $ 40,463.84 | 184 | $ 31,817.72 | 132 | $ 22,825.76 | 80.9 | $ 13,989.42 | |
| 1/2" | 600 | $ 103,753.44 | 506 | $ 87,498.73 | 415 | $ 71,762.80 | 324 | $ 56,026.86 | 235 | $ 40,636.76 | 144 | $ 24,900.83 | |
| 5/8" | 910 | $ 157,359.8 | 790 | $ 136,608.70 | 649 | $ 112,226.64 | 508 | $ 87,844.58 | 366 | $ 63,289.60 | 225 | $ 38,907.54 | |
| 3/4" | 1315 | $ 227,392.96 | 1138 | $ 196,785.69 | 934 | $ 161,509.52 | 729 | $ 126,060.43 | 528 | $ 91,303.03 | 323 | $ 55,853.94 | |
| 7/8" | 1789 | $ 309,358.17 | 1549 | $ 267,856.80 | 1272 | $ 219,957.29 | 994 | $ 171,884.87 | 718 | $ 124,158.28 | 440 | $ 76,085.86 | |
| 1" | 2338 | $ 404,292.57 | 2023 | $ 349,822.02 | 1661 | $ 287,224.11 | 1299 | $ 224,626.20 | 938 | $ 162,201.21 | 575 | $ 99,430.38 | |

State Electricity Coefficients

| State | Net Electrical Generation MWH | Sulfur Dioxide 1000 Metric tons | Nitrogen Oxide 1000 Metric tons | Carbon Dioxide 1000 Metric tons | Sulfur Dioxide Pounds | Nitrogen Oxide Pounds | Carbon Dioxide Pounds | Emission Coefficient Sulfur Dioxide Lbs/KWH | Emission Coefficient Nitrogen Oxide Lbs/KWH | Emission Coefficient Carbon Dioxide Lbs/KWH |
|---|---|---|---|---|---|---|---|---|---|---|
| Other | 0 | 0 | 0 | 0 | 0 | 0 | 0 | #DIV/0! | #DIV/0! | #DIV/0! |
| Alabama | 140895441 | 458 | 122 | 85116 | 1009700176 | 268959435.6 | 1.87646E+11 | 0.0072 | 0.0019 | 1.3318 |
| Alaska | 6674197 | 4 | 18 | 4585 | 8818342.152 | 39682539.68 | 10108024691 | 0.0013 | 0.0059 | 1.5145 |
| Arizona | 104392528 | 45 | 75 | 53353 | 99206349.21 | 165343915.3 | 1.17621E+11 | 0.0010 | 0.0016 | 1.1267 |
| Arkansas | 52168703 | 82 | 38 | 28494 | 180776014.1 | 83774250.44 | 62817460317 | 0.0035 | 0.0016 | 1.2041 |
| California | 216798688 | 27 | 91 | 59389 | 59523809.52 | 200617284 | 1.30928E+11 | 0.0003 | 0.0009 | 0.6039 |
| Colorado | 50698353 | 59 | 66 | 41847 | 130070546.7 | 145502645.5 | 92255291005 | 0.0026 | 0.0029 | 1.8197 |
| Connecticut | 34681736 | 5 | 9 | 11057 | 11022927.69 | 19841269.84 | 24376102293 | 0.0003 | 0.0006 | 0.7029 |
| Delaware | 7182179 | 30 | 11 | 5885 | 66137566.14 | 24250440.92 | 12973985891 | 0.0092 | 0.0034 | 1.8064 |
| District of Columbia | 81467 | 0 | 0 | 99 | 0 | 0 | 218253968.3 | 0.0088 | 0.0097 | 2.6790 |
| Florida | 237751621 | 329 | 212 | 126529 | 725308642 | 467372134 | 2.78944E+11 | 0.0032 | 0.0021 | 1.2467 |
| Georgia | 138010208 | 685 | 130 | 89898 | 1510141093 | 286596119.9 | 1.98188E+11 | 0.0109 | 0.0021 | 1.4360 |
| Hawaii | 11559174 | 22 | 29 | 9036 | 48500881.83 | 63932980.6 | 19920634921 | 0.0042 | 0.0055 | 1.7234 |
| Idaho | 13386085 | 5 | 2 | 875 | 11022927.69 | 4409171.076 | 1929012346 | 0.0008 | 0.0003 | 0.1441 |
| Illinois | 192426958 | 309 | 122 | 99479 | 681216931.2 | 268959435.6 | 2.1931E+11 | 0.0035 | 0.0014 | 1.1397 |
| Indiana | 130489788 | 758 | 202 | 121950 | 1671075838 | 445326278.7 | 2.68849E+11 | 0.0128 | 0.0034 | 2.0603 |
| Iowa | 45483462 | 132 | 64 | 40577 | 291005291 | 141093474.4 | 89455467372 | 0.0064 | 0.0031 | 1.9668 |
| Kansas | 45523736 | 101 | 74 | 35639 | 222663139.3 | 163139329.8 | 78569223986 | 0.0049 | 0.0036 | 1.7259 |
| Kentucky | 98792014 | 391 | 158 | 93160 | 861992945.3 | 348324515 | 2.05379E+11 | 0.0087 | 0.0035 | 2.0789 |
| Louisiana | 90921829 | 125 | 90 | 54098 | 275573192.2 | 198412698.4 | 1.19264E+11 | 0.0030 | 0.0022 | 1.3117 |
| Maine | 16816173 | 17 | 10 | 5635 | 37477954.14 | 22045855.38 | 12422839506 | 0.0022 | 0.0013 | 0.7387 |
| Maryland | 48956880 | 271 | 62 | 30497 | 597442680.8 | 136684303.4 | 67233245150 | 0.0122 | 0.0028 | 1.3733 |
| Massachusetts | 45597775 | 49 | 22 | 23708 | 108024691.4 | 48500881.83 | 52266313933 | 0.0024 | 0.0011 | 1.1462 |
| Michigan | 112556739 | 327 | 113 | 75633 | 720899470.9 | 249118165.8 | 1.66739E+11 | 0.0064 | 0.0022 | 1.4814 |
| Minnesota | 53237789 | 94 | 85 | 37565 | 207231040.6 | 187389770.7 | 82815255732 | 0.0039 | 0.0035 | 1.5556 |
| Mississippi | 46228847 | 82 | 45 | 25802 | 180776014.1 | 99206349.21 | 56882716049 | 0.0039 | 0.0021 | 1.2305 |

ULTRASONIC GAS LEAK DETECTOR WITH AN ELECTRICAL POWER LOSS AND CARBON FOOTPRINT OUTPUT

RELATED APPLICATIONS

The present application claims the benefit of priority under 35 U.S.C. §120 as a continuation-in-part of U.S. patent application Ser. No. 11/339,811 filed on Jan. 24, 2006, now abandoned entitled "General Purpose Signal Converter," which is also a continuation-in-part of U.S. patent application Ser. No. 10/386,008, filed on Mar. 11, 2003, now U.S. Pat. No. 6,996,030, entitled "Apparatus and Method for Minimizing Reception Nulls in Heterodyned Ultrasonic Signals," which is a continuation-in-part of U.S. patent application Ser. No. 10/292,799, filed on Nov. 12, 2002, now U.S. Pat. No. 6,707,762, entitled "System and Method for Heterodyning an Ultrasonic Signal. Each of these prior applications is incorporated herein by reference in its entirety.

BACKGROUND OF THE INVENTION

1. Field of the Invention

The invention generally relates to the field of ultrasonic detectors and, more particularly, to a system using ultrasonic detectors to monitor leaks of compressed gas.

2. Description of the Related Art

It is well known that ultrasonic generators and detectors can be used to locate leaks or defects, e.g., in pipes. Such a system is shown in U.S. Pat. No. 3,978,915 to Harris. In that arrangement, ultrasonic generators are positioned in a chamber through which the pipes pass. At the ends of these pipes, exterior to the chamber, ultrasonic detectors are located. At the point where a leak occurs in the pipe or the pipe wall is thin, the ultrasonic energy will enter the pipe from the chamber and travel to the end of the pipe where the detector is located. The detector will receive an ultrasonic signal at the end of the pipe indicating the existence of the leak or weak spot in the pipe.

Since ultrasonic energy used for these purposes is generally in the range of 40 kHz, it is too high in frequency to be heard by a human being. Thus, means are typically provided for heterodyning, or frequency shifting, the detected signal into the audio range, and various schemes are available for doing this.

When using ultrasonic energy to detect leaks, it is useful to have an ultrasonic detector which indicates the presence and intensity of ultrasonic energy both visually and audibly. U.S. Pat. No. Re. 33,977 to Goodman et al. discloses an ultrasonic sensor that displays the intensity of the detected signal on an output meter operable in either linear or logarithmic mode, and also provides for audio output through headphones. U.S. Pat. No. 4,987,769 to Peacock et al. discloses an ultrasonic detector that displays the amplitude of the detected ultrasonic signal on a ten-stage logarithmic LED display. However, the detector disclosed in Peacock does not process the detected signal to produce an audible response, nor does it provide for signal attenuation after the initial pre-amplification stage.

Whenever there is a leak of compressed gas, it typically must be made up by generating more compressed gas in order to keep the relevant industrial process operating correctly. Knowing the operating parameters of the compressor used to generate the compressed gas, it is possible to calculate the amount of electricity that is needed for this purpose, and hence the amount of electrical energy that is wasted as a result of the leak.

When compressors are located throughout a large industrial site, it is most common to have personnel walk throughout the plant with a battery powered handheld detector making readings and storing the dB value and the location of the measurement in the detector. They return to a central location were the information is downloaded to a computer. However, it is disclosed in applicants' U.S. Pat. No. 11/339,811 filed on Jan. 24, 2006 to monitor the compressors by remote ultrasonic detectors, whose outputs are fed back by wire or wirelessly to a common monitoring location. Thus, the site operator can dispatch a repair crew to locations were the detectors indicate a leak is occurring. However, it may not be cost efficient to dispatch a repair crew to fix every leak. Depending on its size, the value of the electricity needed to compensate for the leak may be much smaller than the cost of the repair crew. In such a case, the leak may be noted for repair during routine maintenance or during a repair mission in the area for some other reason.

Making the decision about whether it is cost effective to send an immediate repair crew can be difficult and time consuming itself Thus, a detector which provides an output in terms of energy loss would be valuable to the site operator, not only in determining the effect of a single compressed gas leak, but in determining the cost of multiple leaks throughout the site.

With the recent acceptance of global climate change as a result of carbon dioxide emissions, various proposals have been made as to how industrial sites are to be monitored for their effect on the environment. One such proposal envisioned by the Kyoto Protocol involves the determination of the carbon footprint of an enterprise (i.e., a measure of the amount of carbon dioxide ($CO_2$) and other greenhouse gases emitted by the enterprise, the setting of a limit on the footprint, and the possibility of trading carbon credits between enterprises that are below their carbon footprint with those which are above, so that an acceptable average is reached.

The generation of electricity to drive a compressor to replace leaking compressed gas results in an increase in carbon dioxide in the air, assuming the electricity is generated by carbon based fuels such as coal or oil, as opposed to nuclear energy. Thus, a relevant consideration for a site operator receiving information about a compressed gas leak is not only whether the cost to repair it exceeds the cost for the electricity to replace it, but whether this additional electricity would put the site close to exceeding its allowable carbon footprint. As with the calculation of the electrical energy loss by the leak, the carbon footprint effect can be very difficult for a site operate to determine.

SUMMARY OF THE INVENTION

The present invention is directed to providing improved methods and apparatus for detecting gas leaks by ultrasonic means, and reporting those leaks as electrical energy required to replace the lost gas over some time period and the effect of the additional need for electricity on the carbon footprint of the facility.

In accordance with the invention, ultrasonic detectors are used to read and store information about compressed gas leak readings in decibels, dB. The inventors have discovered that there is a rough correlation between the amplitude of the ultrasonic signal in dB and the size of the leak in cubic feet per minute ("cfm") of leaked gas. By means of charts and software, the stored ultrasonic dB reading is converted to an approximate flow rate of loss compressed gas (cfm). This value can in turn be converted to the amount of electricity needed to generate enough additional gas to make up for the loss compressed gas. In particular, a chart, but more usefully software, is used to covert the cfm to kilowatt hours ("kWh"), so that the system can present the user with a kwh per leak value. This conversion depends on the amount of electricity needed to compress the particular type of gas that is leaking and the efficiency of the compressors that generate the compressed gas. Further, given the kWh value, a chart or software can convert the reading to greenhouse gas emissions per leak. This, of course, depends on the type of electrical power generation that is used.

If the facility generates its own electricity, a precise value can be obtained. However, where electricity is purchased over the electrical power grid, the electric generators connected to the grid and their environmental impact can vary greatly. For example, a coal-fired generator and a nuclear generator may both supply electrical power to the grid. However, an average value of environmental impact of electrical generation can be obtained on a state-by-state basis.

The present inventions permits the value of individual leaks to be determined in terms of electrical usage, cost of electricity and/or carbon emissions. Further, the user can track value of the total of all leaks. Further, any trends can also be determined. In a preferred embodiment, this information is automated based on the dB output of ultrasonic detection instruments and can result in a report of the results.

In another embodiment, the report may be web based so that individual and total results for a site, a division or an enterprise can be tracked remotely. In addition, if industry averages are posted, a company can track its performance versus a baseline average.

Currently, customers who are interested in carbon emission and how to reduce them, focus on more efficient lights or maybe more efficient compressors etc. With the present invention, the customer can use the ultrasound detection to measure creation of green house gases per leak of compressed air, thus providing a way to for the customer to start taking action to reduce those gases without large capital expense.

BRIEF DESCRIPTION OF THE DRAWINGS

The foregoing and other advantages and features of the invention will become more apparent from the detailed description of the exemplary embodiments of the invention given below with reference to the accompanying drawings in which:

FIG. 10A is a Flow Rate Table that provides a rough correlation between the ultrasonic detector reading in dB, the approximate leak rate and the cost to replace the leaking gas;

FIG. 10B is a table that correlates the size of a leak to the dB and the cost; and FIG. 11 is a Coefficient Table that provides a rough correlation between electricity generated in a state and the emission of environmentally harmful gases as a result of that generation.

DETAILED DESCRIPTION OF AN EXEMPLARY EMBODIMENT

Figure 1:
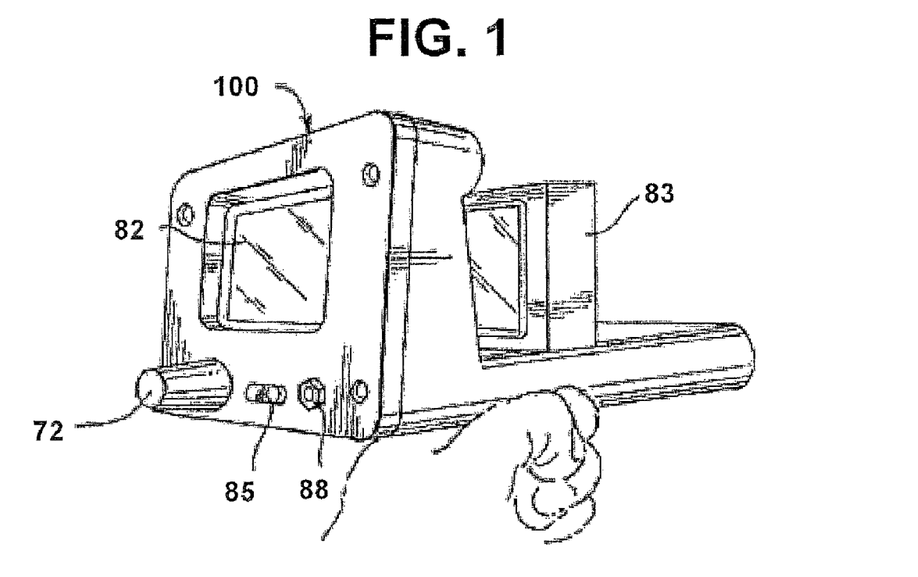
FIG. 1 is a perspective view showing the rear panel of an ultrasonic instrument useful with the present invention.

FIG. 1 is a perspective view of a portable ultrasonic detector 100. Toward the front of the housing there are ultrasonic transducers (not shown). Micro-processor controlled circuits for heterodyning the ultrasonic signal to shift its frequency to the audio range are contained in the body of the housing. A display 82, e.g., an LCD, is located at the back so the operation and the results can be viewed. At the back, there is also a jack 88 for headphones, so that the user can listen to the audio sound during a test, e.g., as a way of locating a leak. Other jacks and controls are located on the body.

In the contemplated embodiments of the invention, the LCD screen (FIG. 2) is large so that the display can easily be seen by the operator. In accordance with the contemplated embodiments, this would include a time series display of the heterodyned ultrasonic signal to permit the viewing of measurement trends in real time.

The dB output signal at a connector on the bottom of the detector (not shown) has a 50 dB dynamic range, a 0-5V DC scale for direct input to a micro-controller, and an accurate linear dB format. The sensitivity of the detector is adjusted by turning a rotational knob 72 that is located at the back of the housing. In preferred embodiments, the sensitivity encoder 100 is a rotational optical encoder.

Figure 2:
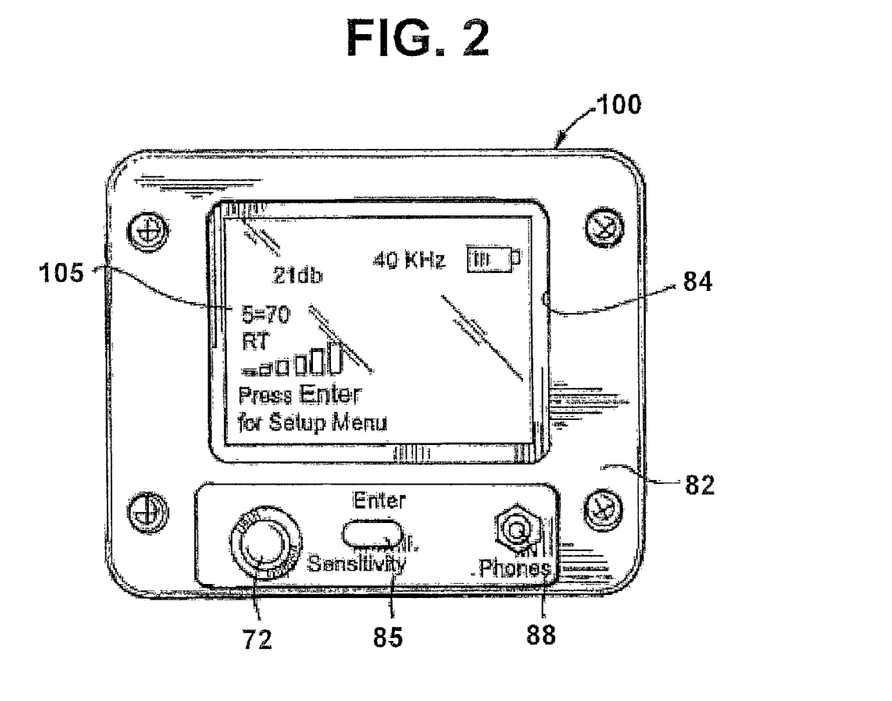
FIG. 2 is a plan view of the rear panel of the ultrasonic instrument of the invention.

LCD 82 provides a display of data that is used to distinguish between trends or deviations in readings. As a result, a user is provided with the means to pinpoint an ultrasonic source, such as an internal leak in a tank or vessel, or an underground leak in gas piping or electrical transmission lines.

Sensitivity level indicator 105, shown on the LCD 82, provides the user with the ability to view the sensitivity level setting of the heterodyne circuit. As a result, the user can consistently set the sensitivity level of the circuit to permit repeated comparative frequency spectrum measurements, where repeatability is critical. LCD 82 displays the sensitivity level setting as a range of integer numbers. In the preferred embodiment, this range is from 0 to 70S, where S is an abbreviation for sensitivity.

In accordance with the invention, the integer numbers represent the adjustment range, where each integer value corresponds to one decibel in the change of the gain. In accordance with the preferred embodiment, a sensitivity level setting of 70 corresponds to maximum sensitivity while a sensitivity level setting of 0 corresponds to a minimum sensitivity setting (70 dB below maximum sensitivity). In accordance with the invention, the sensitivity setting is also a field in the memory of the portable ultrasonic detector so that when the user presses the Enter button 85, the sensitivity level setting value is stored. In certain embodiments of the invention, the user can also annotate data files that are stored and, by way of voice recognition, incorporate them into a final report.

In accordance with the invention, "Spin and Click™" controls are used to provide an end user interface that is simple and intuitive. With reference to FIG. 2, knob 72 acts as a cursor control. As knob 72 is clicked, the cursor moves in a set pattern around the display screen 82. If a "function field" is blinking, knob 72 is then spun to change the values within the function field. Once a function is selected, knob 72 is then clicked to set the selected value.

In accordance with the preferred embodiment of the invention, multiple applications can be run on the detector. In the preferred embodiment, there are 6 applications, i.e., GENERIC, LEAKS, STEAM TRAPS, VALVES, BEARINGS AND ELECTRICAL. Each application has two screens, i.e., MAIN and STORAGE. The "Click" on knob 72 moves the "cursor" to "FIXED" positions on each screen. In certain embodiments, the number of controls are minimized; but, in the preferred embodiment, two controls are used to permit the user to "navigate" through the various display screens, and change multiple operational settings.

Figure 3:
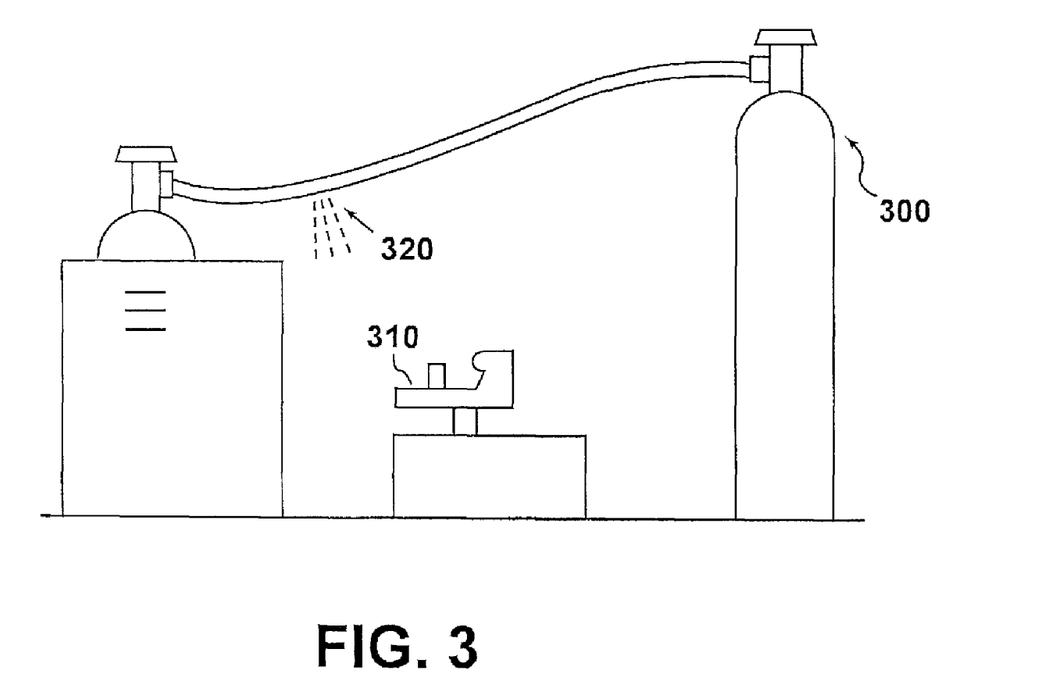
FIG. 3 is a view of the ultrasonic detector located to remotely detect the leakage of compressed gas.
Figure 4:
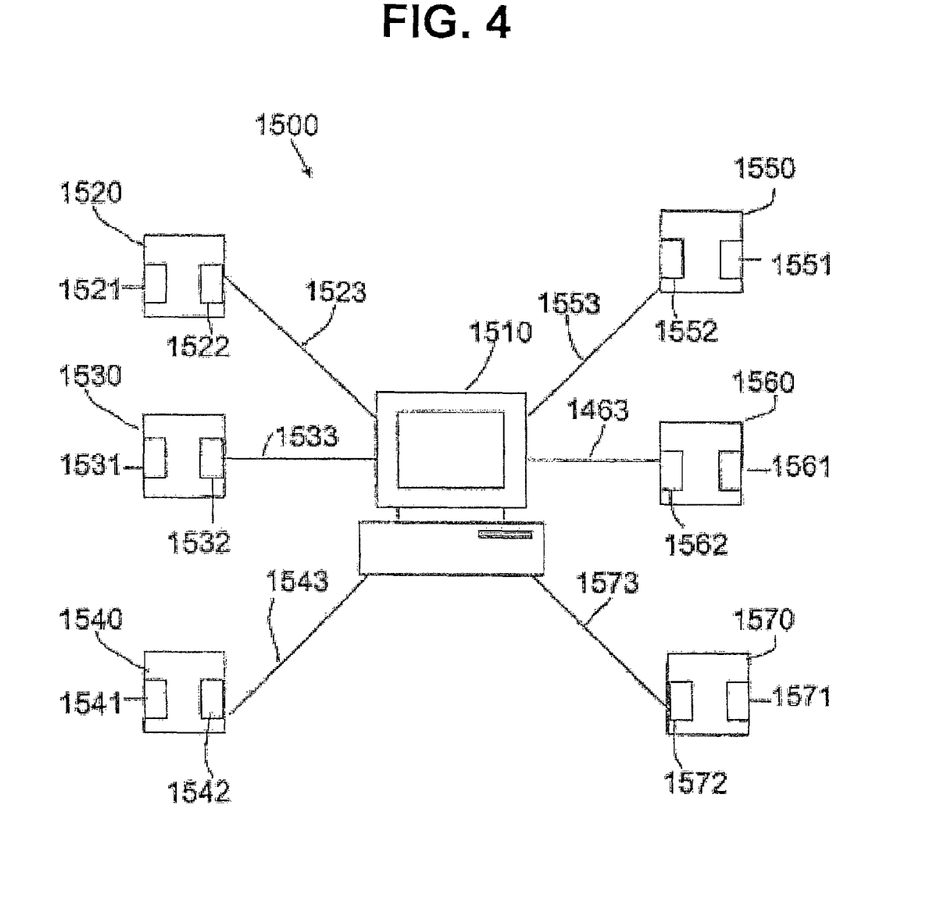
FIG. 4 is a block diagram illustrating a plurality of ultrasonic detectors used for remote monitoring of compressed gas reservoirs located throughout a facility.

FIGS. 3 and 4 are directed to an embodiment of the present invention in which the ultrasonic detector is placed in a remotely located position next to a reservoir, e.g., a tank 300, of compressed gas to monitor whether there is a leak 320. By remotely mounting the ultrasonic detector 310 an inspector does not need to periodically travel to remote locations to conduct ultrasonic tests to determine if the gas is leaking or whether there is a need for maintenance. However, spaced-apart visits are still recommended.

FIG. 4 is a block diagram illustrating a system 1500 in which the ultrasonic detector are used for remote monitoring of gas reservoirs. The system 1500 includes a plurality of ultrasonic detectors 1520, 1530, 1540, 1550, 1560, 1570 located at respective gas reservoirs. The ultrasonic detectors 1520 . . . 1570 detect ultrasonic emissions generated by leaks of compressed gas, and heterodyne the ultrasonic emissions into audio signals proportional to the received ultrasonic emissions. While six ultrasonic detectors 1520 . . . 1570 are shown, any number of ultrasonic detectors may be included in the system.

The ultrasonic detectors 1520 . . . 1570 include respective failure condition detectors 1521, 1531, 1541, 1551, 1561, 1571, which can in real-time detect a potential leak condition when the audio signal falls outside of a predetermined profile. Digital audio network converters 1522, 1532, 1542, 1552, 1562, 1572 convert the audio signal into a digital audio stream, which is transmitted via an Ethernet connection (not shown) in either half or full duplex mode. The converters 1522 . . . 1572 and the failure condition detectors 1521 . . . 1571 may be located with the ultrasonic detectors 1520 . . . 1570 or they may be provided in separate housings. Moreover, a user is able to set the IP address of the digital audio network converter 1522 . . . 1572 for use in single point-to-point systems or for use in multiple detector systems using LAN networks or router-based systems.

The digital audio stream can be generated and transmitted continuously, only when a potential leak condition is detected, at periodic intervals for regular testing, or anytime testing of a compressed gas reservoir is desired. Also, the user can start and stop the digital audio stream using control signals transmitted via the Ethernet connection to the ultrasonic detector 1520 . . . 1570.

A processing unit 1510 is centrally located remotely to receive inputs from the ultrasonic detectors 1520 . . . 1570. Transmitting lines 1523, 1533, 1543, 1553, 1563, 1573 transmit the digital audio stream to the processing unit 1510. Thus, it is not merely an alarm signal that is sent to the central processing unit 1510, but a digitized version of the audio frequency signal that is representative of the ultrasonic emissions. The transmitting lines 1523 . . . 1573 can be "hard wired" (e.g., Ethernet, cable, internet, etc.) or wireless (e.g., radio spectrum, Wi-Fi, cell phone, etc.).

The ultrasonic detectors 1520 . . . 1570 as well as the processing unit 1510, can have an embedded local internet server for remote network web browser access/monitoring. Also, when a failure condition is detected by the failure condition detector 1521 . . . 1571, an e-mail can be sent to the central processing unit 1510 or any other address.

After the digital audio stream is received at the central processing unit 1510, an expert can use the processing unit 1510 to analyze the digital audio stream to determine whether the potential failure condition is an actual failure condition or is caused by a false event, such as a competing source. That is, the processing unit 1510 can use analysis software to determine whether the signal represents an actual compressed gas leak. This can be based on the frequency spectrum of the signal. Also, the inspectors can simultaneously hear the digital audio stream while viewing the streams on a screen. When compared with a known "good" or "normal" profile, an anomaly can be quickly determined.

Figure 5:
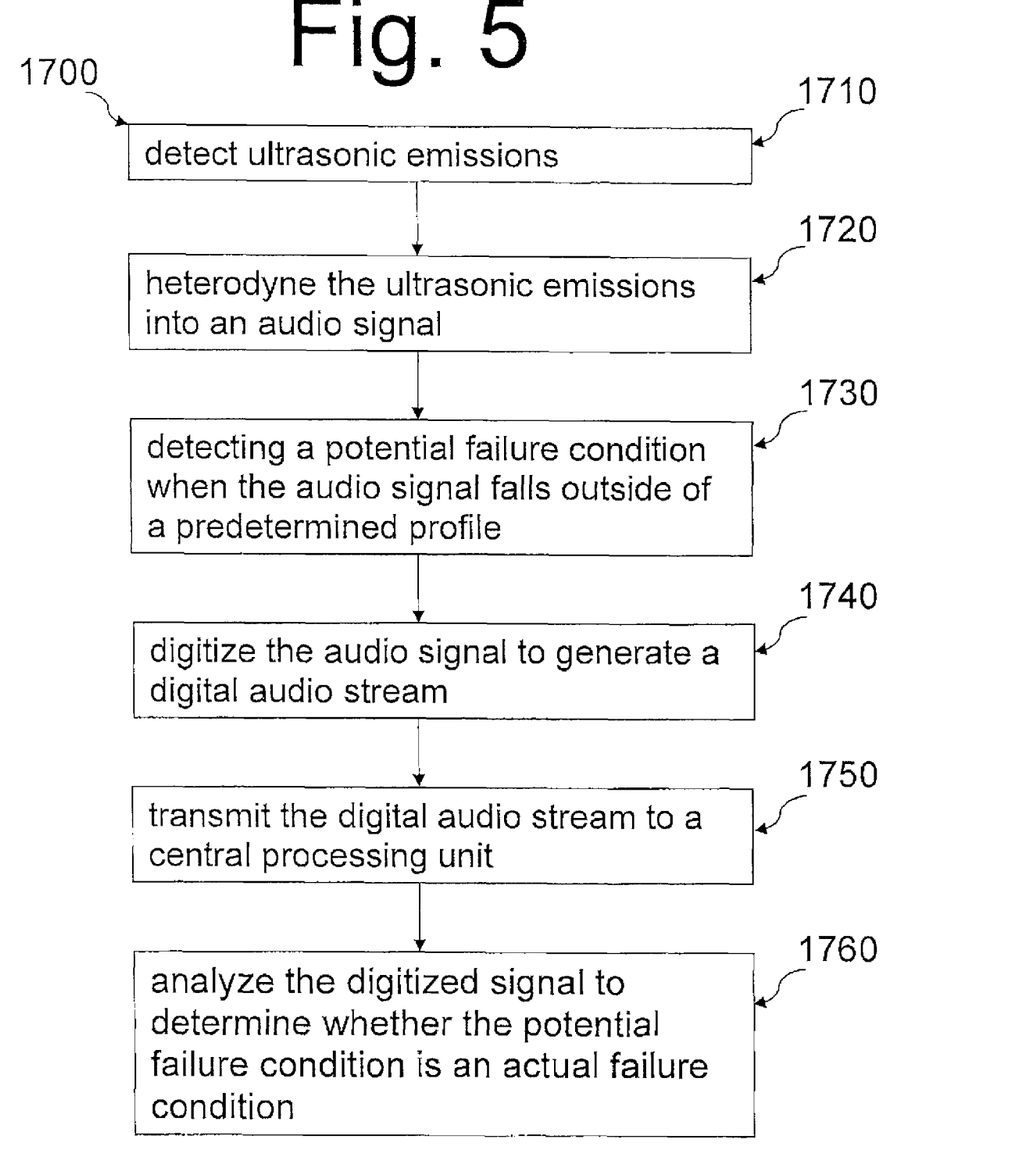
FIG. 5 is a flowchart illustrating the operation of the remote monitoring of compressed gas leaks.

FIG. 5 is a flowchart 1700 illustrating the operation of the remote monitoring of the compressed gas reservoirs. First, an ultrasonic detector 1520 . . . 1570 detects ultrasonic emissions generated by the leaking gas (step 1710). The ultrasonic detector 1520 . . . 1570 then heterodynes the ultrasonic emissions into an audio signal (step 1720). The failure condition detector 1521 . . . 1571 detects a potential failure condition when the audio signal falls outside of a predetermined profile (step 1730). When a potential failure condition, i.e., a leak of compressed gas, is detected, the audio signal is digitized to create a digital audio stream (step 1740). The digital audio stream, rather than or in conjunction with an alarm, is then transmitted to the central processing unit 1510 located remotely from the gas reservoir at the ultrasonic detector 1520 . . . 1570 (step 1750). Finally, the processing unit 1510 analyzes the digital audio stream to determine whether the potential failure condition is an actual failure condition (step 1760). If there is an actual failure condition, the processing unit 1510 could send a control signal to the gas reservoir to shut down its operation. However, according to the present invention, the processor 1510 can analyze the signal to determine the rate of flow of the leak, and in turn calculate the amount of electrical energy per unit time it would take to replace the leaking gas, as well as the carbon footprint or carbon load created by the replacement of the leaking gas.

Figure 6:
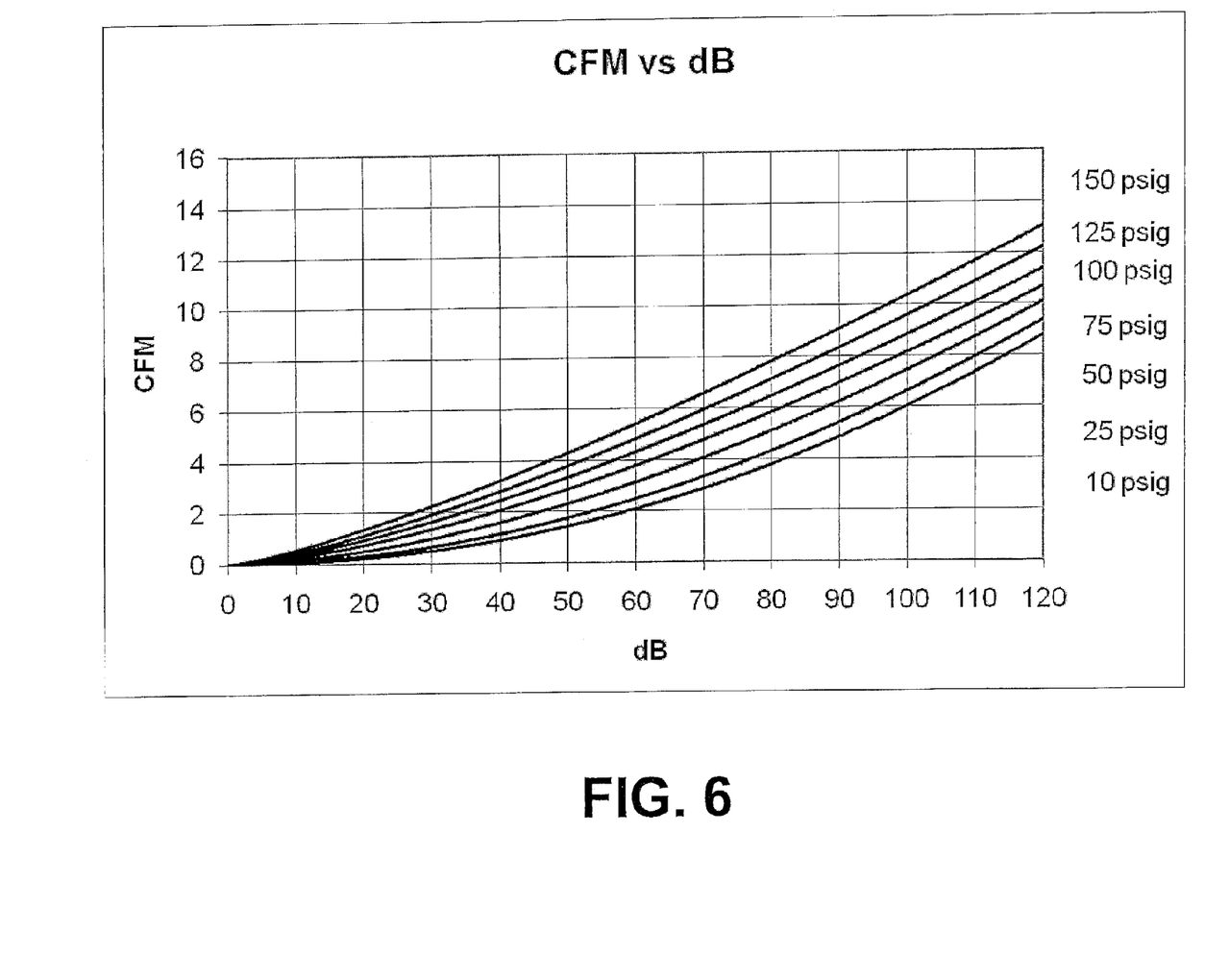
FIG. 6 is a chart showing the relationship between the amplitude of the ultrasonic signal in dB versus the flow rate in cubic feet per minute of a leak of compressed gas that created the ultrasonic signal.

FIG. 6 is a graph of a set of curves which shows the relationship between flow rate in cubic feet per minute (cfm) and the ultrasonic signal amplitude in decibel (dB) level for leaks of compressed gas at specific pressure levels. The values in the flow rate table were empirically determined and statistically trended for the best fit relationships. Since at least the initial set gas pressure is known for any gas reservoir at a facility, the flow rate can be determined rather accurately. Naturally, if the leak persists over a long period of time or is at an exceptionally high rate, the gas pressure will drop and the flow rate calculation will be somewhat less accurate.

The values in FIG. 6 can be programmed into the processor 1510 of FIG. 4, so that for each detector 1520 . . . 1570, the processor can calculate the flow rate of any leak detected by it. This flow rate can be displayed on the monitor of processor 1510 so that an operator can immediately see the rate of gas leakage at one or all of the gas reservoirs of a facility, and can make operational decisions as a result thereof. Such decisions can include anything from ignoring the leak because it is too small to be significant to halting the operation of the facility By centralizing the calculation of the flow rate of the leak, as well as the information that can be determined from it, e.g., electricity cost and carbon footprint, commercially available ultrasonic detectors, e.g., the UE System's UltraProbe™ series of instruments, can be used to carry out the invention without modification. However, it is also contemplated that the software and computing power for making these determinations could be incorporated into individual ultrasonic detectors.

One piece of information provided by the present invention that the operator of the facility may find helpful is an estimate of how much money can be saved annually (cost avoidance) by identifying and repairing leaks on a compressed air system. Another piece of useful information is an estimate of the "emission footprint," specifically the carbon footprint (in pounds of carbon dioxide) and the other significant components of the emission footprint created by using electricity to generate compressed air in a compressed gas system that leaks.

Carbon dioxide, nitrogen oxide, and sulfur dioxide are the most significant components of the products of combustion when generating electricity from burning fossil fuels. Emission coefficients are calculated and tabulated by state in the State Electricity Profiles Report from the US Department of Energy, Energy Information Administration Office of Coal, Nuclear, Electric, and Alternative Fuels in terms of Pounds of carbon dioxide per kilo Watt hour (lbs of $CO_2$/kWh), Pounds nitrogen oxide per kilo Watt hour (lbs of NO/kWh), and pounds of sulfur dioxide per kilo Watt hour (lbs of $SO_2$/kWh). This information can also be stored in processor 1510 and used to make the desired calculations. In particular, the Compressed Gas Survey information of FIG. 6 converts the dB level of the ultrasonic leak to a flow rate (cfm) and the Electricity Profiles Report information is used to calculate the cost to generate 1000 cubic feet of air (MCF). The system calculates the cost of the air leaks (cost avoidance) and the emission footprint in lbs of $CO_2$, NO, and $SO_2$ for the facility with the leaks that are not repaired for a specified operation time.

Figure 7:
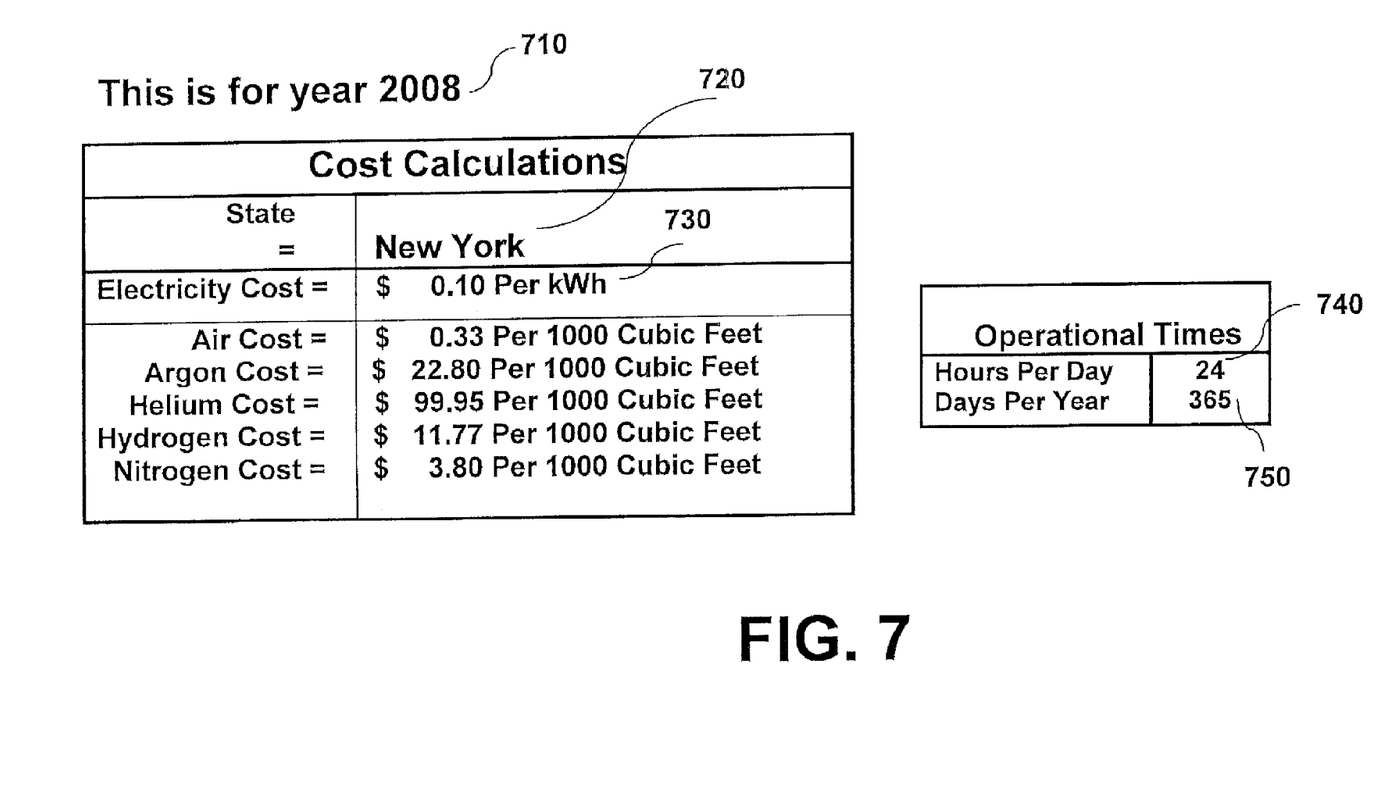
FIG. 7 is a computer interface screen that accepts initial information for use with the present invention.

In operation, an ultrasonic detector, e.g., an Ultraprobe™ is used to measure the ultrasonic dB (decibel) level of a pressurized air leak or leaks. This information is used to calculate the cost of electricity, either at the detector, or a remote processor 1510. In order to prepare the system to make the calculation, a Cost Interface as shown in FIG. 7, is accessed by the user. This interface is used to enter the costs for gases for the year. At location 710 the year, e.g., 2008, is inserted. Then, the user can choose the state from the drop down list at 720 and enter the cost of electricity at 730 to automatically calculate the cost of an air leak per 1000 cubic feet (e.g., $0.33) and to enable the generation of environmental impact estimations. If the state/region is not listed, the user can select "Other" and complete the blank cells at the top of the Coefficient Table of FIG. 11.

FIG. 11 is a State Electricity Coefficients chart which lists this information by state. Column 1101 lists the names of the states. Column 1102 indicates the net electrical power generation of each state. In column 1103-1105 the sulfur dioxide, nitrogen oxide and carbon dioxide emitted from the electrical generating capacity in the state are listed in 1000 metric ton units. Columns 1106-1108 provide the same information in pounds. Columns 1109-1111 indicate the emission efficiency for each gas, i.e., the mass of the gas divided by the total electrical generation in terms of kWhs.

As an alternative to automatically generating the cost of an air leak, the user can enter his or her cost for 1000 cubic feet of air and manually enter the Argon, Helium, Hydrogen and Nitrogen costs in the state. Changing these values updates the entire electronic spreadsheet.

While some facilities operate all the time, others have specific operating times. Thus, in order to make accurate calculations it may be necessary to enter into the system the "operation time", i.e., the number of hours per day 740 and number of days of operation in a year 740 that the compressors are in operation. This information may be entered into the interface of FIG. 7.

Figure 8:
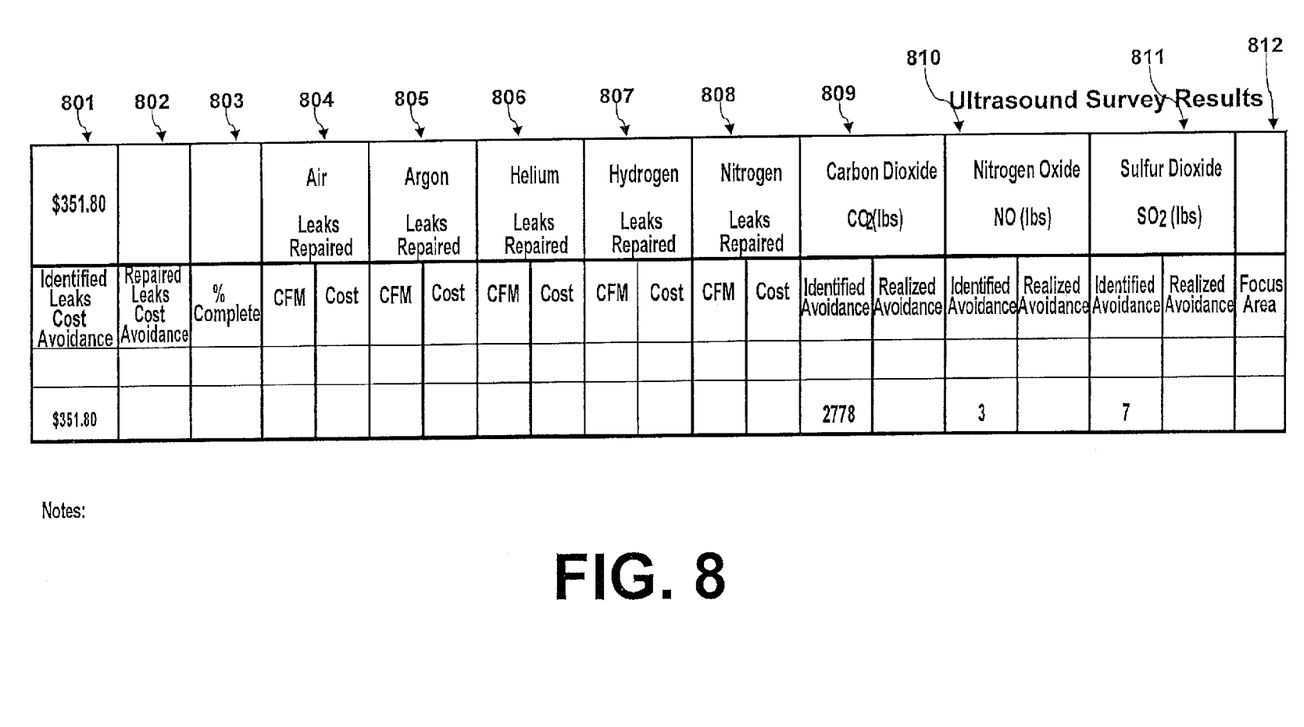
FIG. 8 is a Report worksheet screen used to record and display compressed gas leaks detected for the year.

The Report Worksheet screen of FIG. 8 is used to tabulate all of the leaks found for the year. The first column 801 identifies the cost of the leak, i.e., the expense that can be avoided if the leak is repaired. The next column 802 provides the cost savings for leaks that were repaired. Column 803 gives the percentage of leaks that have been repaired. For each of air, argon, helium, hydrogen, nitrogen, the columns 804-808 list the flow rate of the detected leak and the cost of each gas. The next columns 809-811 are for the identified and realized avoidance for carbon dioxide, nitric oxide and sulfur dioxide, respectively. The last column, the "Focus Area" 812 is the location of leak. Below the listings there is a space reserved for notes.

Figure 9:
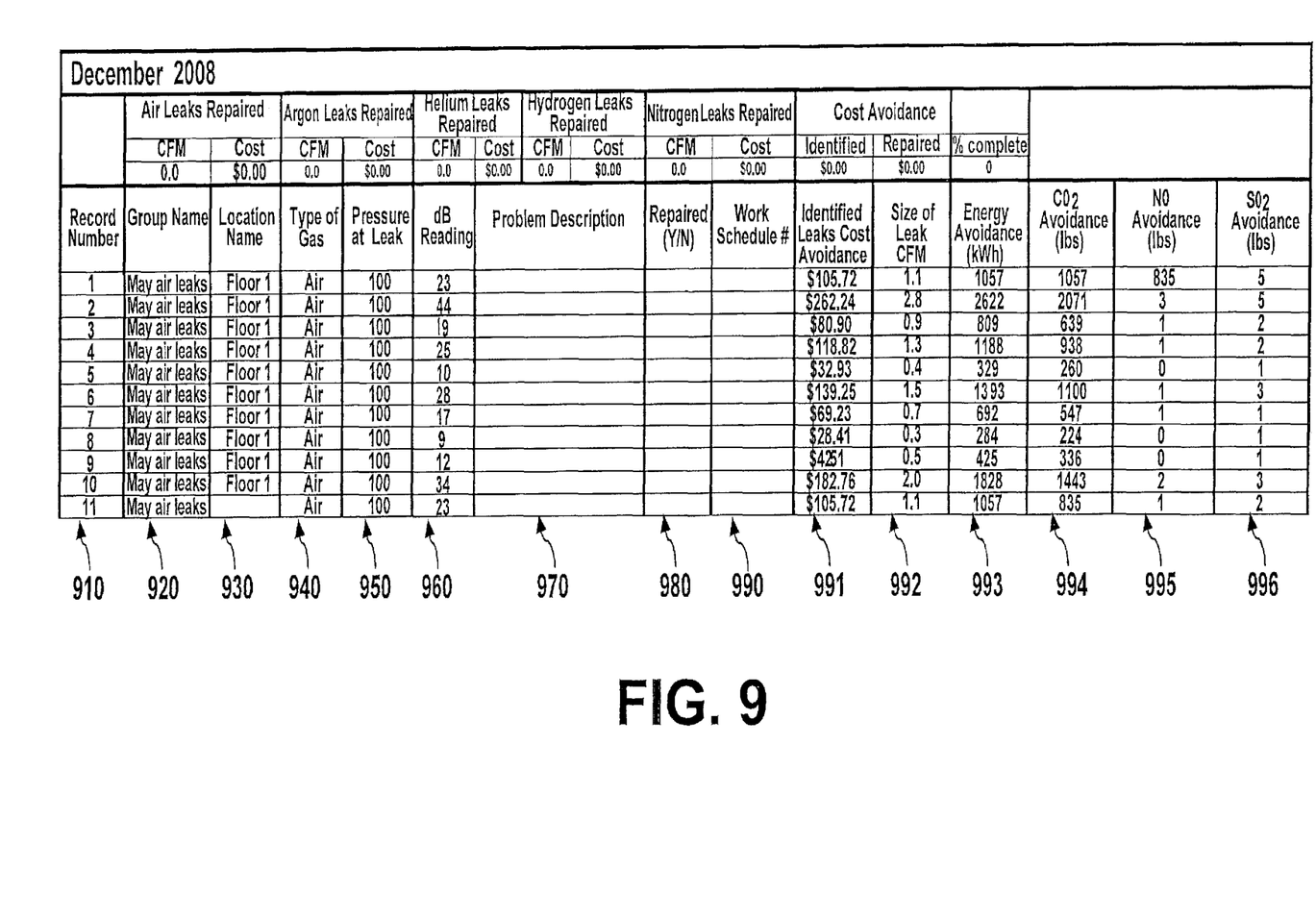
FIG. 9 is a Monthly worksheet screen used to record and display compressed gas leaks detected for the month and whether they have been repaired.

January-December Worksheet Sheet interface screens are used to record the leaks detected in a month and to indicate if they have been repaired. An example for the month of May is shown in FIG. 9. The monthly information automatically updates the information in the Report Worksheet of FIG. 8.

The first six columns 910, 920, 930, 940, 950, 960 of FIG. 9 indicate the number of the record, the Group Name (e.g., Air Leaks for May), the location of the compressed gas reservoir, the type of gas, the pressure and the dB reading from the ultrasonic detector at that location. The type of gas and the gas pressure can be input by means of drop down menus. Drop down menus can be also used to assist in making other entries.

The problem that caused the leak can be entered in the next column, 970. Under the "repaired" and "Work Order" columns 980, 990, the operator can indicate whether the leak has been repaired and the work order schedule number for the leak. Importantly, the next two columns 991, 992 indicate the amount saved by fixing the leak and the size of the leak. This is calculated from the dB reading and the pressure, according to the information in the chart of FIG. 6. The energy in kilowatt hours (kWh) is indicated in column 993. Finally, the amount of $CO_2$, NO and $SO_2$ emissions eliminated by repair of the leak are indicated in the last three columns, 994, 995, 996 for compressed air only.

Along the top of FIG. 9 there is a summary of the input information. It provides the flow rate and cost of all leaks repaired, as well as similar information for each of the gases. The last entries provide information on the leaks identified, repaired and the percentage complete.

When the ultrasonic dB level of the leak or leaks is entered into the system from the ultrasonic detectors, the dB measurement is converted into a flow rate according to the chart of FIG. 6 and an associated "cost avoidance in $" of that leak for a specific pressure and for the entered operational time is calculated. In order to provide efficient processing to the information in FIG. 6, it is converted to a table as shown in FIG. 10A. In FIG. 10A the dB reading is provided in column 1001. Then the corresponding leak rate is provided in column 1002 and the cost is provided in column 1003 for gas at a pressure of 150 pounds-per-square inch (psi). FIG. 10A provides values for increasing dB readings and for different pressures. In FIG. 10A the gas is compressed Air.

FIG. 10B shows the end of the chart which begins in FIG. 10A, as well as a table 1020 which provides correspondence between a leak rate, the diameter of the leak and the costs for different pressures.

The total kilo Watt hours (kWh) required to run the compressors and to maintain the pressure given the measured leak or leaks for the entered operational time is calculated by dividing the "cost avoidance in $" by the cost of electricity in $/kWh.

The total pounds (lbs) of $CO_2$, NO, and $SO_2$ generated (the emission footprint) for a specific operational time to run and maintain a pressure in a compressed air system with the identified leak or leaks is calculated by multiplying the Emission coefficients for $CO_2$, NO, and $SO_2$ (lbs/kWh) by the total Kilo Watt Hours (kWh).

These calculations for compressed air only are based on the following formulas:

Cost of 1000 cubic feet of air, $ per MCF:

$$\$ \text{ per MCF} = N(\$/h)/D(\text{MCF}/h)$$

$$N(\$/h) = (\text{BHP}/0.9)*(0.746 \text{ kW/BHP})*(\$/\text{kWh})$$

$$D(\text{MCF}/h) = (\text{BHP})*(4.2 \text{ cfm/BHP})*(60 \text{ min}/h)/(1000 \text{ CF/MCF})$$

Where:
CF=Cubic feet of air
MCF=1000 cubic feet of air
CFM=Cubic feet per minute
BHP=Break Horse power of the air compressor
min=Minutes
h=Hours
$=Dollars
kW=Kilo Watts
kWh=Kilo Watt Hours
0.9=Efficiency of the compressor
4.2 CFM/BHP=An average of cfm per BHP provided by compressor manufacturers $$\$ \text{ per } MCF = 3.29 * (\$ \text{ per kWh})$$

Cost Avoidance per year=(X cubic feet per minute)*(60 minutes per hour)*(Y hours of operation per day)*(Z days of operation per year)*($ per 1000 cubic feet of any gas)

By using the present invention the value of individual leaks can be determined in terms of electrical usage, cost of electricity and/or carbon emissions. Further, the user can track value of the total of all leaks in a facility or over an entire enterprise. Further, any trends can also be determined. The process can be automated to produce reports based on the dB output of ultrasonic detection instruments. Such reports may be web based so that individual and total results for a site, a division or an enterprise can be tracked remotely. In particular, remote access to processor 1510 can be provided over a private network or the internet. In addition, if industry averages may be posted by processor 1510 so that a company can track its performance versus a baseline average.

Although the invention has been described and illustrated in detail, it is to be clearly understood that the same is by way of illustration and example, and is not to be taken by way of limitation. The spirit and scope of the present invention are to be limited only by the terms of the appended claims.

The invention claimed is:

1. A system for determining the carbon footprint of a compressed gas leak from a compressed gas supply created by an electrical compressor connected to an electrical power generation network, the system comprising:

an ultrasonic detector configured to detect the existence and volume of a compressed gas leak and to generate an electrical signal representative thereof;

a storage device storing information on the type of compressed gas, the efficiency of the compressor creating the compressed gas and the carbon emissions necessary for the electrical power generation network that drives the compressor to generate a unit of electricity;

a processing unit connected to receive the electrical signal and having access to said storage device, said processing unit including a software module configured to determine an amount of electrical energy per unit of time needed to recharge a loss in compressed gas that results from the determined compressed gas leak based on the efficiency of the compressor; and a display connected to the processing unit and displaying the amount of electrical energy associated with the compressed gas leak.

2. The system of claim 1, further including a software module configured to calculate the carbon emissions created by the amount of electrical energy needed to recharge the loss in compressed gas.

3. The system of claim 2, wherein the display is further configured to display the amount of carbon emissions.

4. The system of claim 1 wherein the ultrasonic detector comprises:

a heterodyne circuit configured to shift an ultrasonic signal to an audio signal, a display configured to display a time series representation of the shifted ultrasonic signal, a headphone jack;

a failure condition detector in communication with the heterodyne circuit and configured to determine if the audio signal falls outside a predetermined profile;

a digital audio network converter configured to convert an audio signal outside the predetermined range to a digital data stream and to transmit the digital data stream as an electrical signal representative of the existence and volume of a compressed gas leak.

5. A system for determining the carbon footprint of a compressed gas leak, the system comprising:

an ultrasonic detector including a heterodyne circuit configured to shift an ultrasonic signal to an audio signal, a display configured to display a time series representation of the shifted ultrasonic signal, and a headphone jack;

a failure condition detector in communication with the ultrasonic detector and configured to determine if the audio signal falls outside a predetermined profile;

a digital audio network converter configured to convert an audio signal outside the predetermined range to a digital data stream and to transmit the digital data stream across a communication network; and a processing unit connected to the communication network and configured to receive the digital data stream, the processing unit including an analysis software module configured to determine if the digital data stream represents a compressed gas leak, and to determine the rate-of-flow of the determined compressed gas leak so as to calculate an amount of electrical energy per unit of time needed to recharge a loss in compressed gas that results from the determined compressed gas leak, and the processing unit further including a software module configured to calculate the carbon footprint created by the amount of electrical energy needed to recharge the loss in compressed gas.

6. The system of claim 5, wherein the ultrasonic detector is remotely located from the processing unit and in proximity of a reservoir of compressed gas.

7. The system of claim 5, wherein the ultrasonic detector, the failure condition detector, and the digital audio network converter are located in a single housing.

8. The system of claim 5, wherein the calculated amount of electrical energy is dependent on factors including at least one of a particular type of gas to be compressed, and an efficiency of a gas compressor connected to the reservoir.

9. The system of claim 5, wherein the calculated carbon footprint is dependent on a type of electrical power generation.

10. The system of claim 5, further comprising a plurality of ultrasonic detectors located in proximity to a plurality of respective reservoirs of compressed gas, wherein each of the plurality of ultrasonic detectors is connected to a respective failure condition detector.

11. The system of claim 10, wherein the processing unit receives respective digital data streams representative of an ultrasonic signal from each of the plurality of ultrasonic detectors, the system further comprising a display connected to the processing unit, wherein the display is configured to display at least one of a cumulative amount of electrical energy needed to recharge the plurality of respective reservoirs and a cumulative carbon footprint corresponding to the cumulative amount of electrical energy.

12. The system of claim 5, wherein the processing unit is further configured to generate a report correlating at least one of the determined compressed gas leak to electrical usage, a cost of the electrical usage per unit of time, and a quantity of carbon emissions required to recharge the loss in compressed gas.

13. The system of claim 5, wherein the digital audio network converter is configured to generate the digital audio stream one of continuously, periodically, and in response to detection of a potential compressed gas leak.

14. The system of claim 5, wherein the ultrasonic leak detector further includes an embedded network server for access and remote monitoring.

15. The system of claim 5, wherein the determination by the processing unit of a compressed gas leak is based on a frequency spectrum of the received digital data stream.

16. A method for remotely monitoring for potential gas leaks from a compressed gas reservoir created by an electrical compressor connected to an electrical power generation network and determining the carbon foot print as a result of such gas leaks, the method comprising the steps of:
  detecting ultrasonic emissions from the compressed gas reservoir due to a gas leak;
  generating an electrical signal representative of the existence and volume per unit time of the gas leak; and
  calculating an amount of electrical energy per unit of time needed to recharge a loss in compressed gas resulting from the gas leak, said calculation being based on the efficiency of the compressor.

17. The method of claim 16, further including the step of calculating the carbon footprint created by the gas leak based on the carbon emissions necessary for the electrical power generation system that drives the compressor to generate a unit of electricity.

18. The method of claim 16, wherein the steps of detecting ultrasonic emissions and generating an electrical signal comprise the steps of:
  generating an ultrasonic electrical signal based on the ultrasonic emissions from the compressed gas leak;
  heterodyning the ultrasonic signal into an audio signal;
  providing the audio signal to a failure condition detector that determines if the audio signal falls outside a predetermined profile;
  digitizing, by a digital audio network converter, an audio signal outside the predetermined range to a digital data stream;
  determining with a processor, if the digital data stream represents a compressed gas leak;
  calculating the rate-of-flow of the determined compressed gas leak; and
  generating an electrical signal representative of the existence and volume per unit time of the gas leak.

19. A method for remotely monitoring a compressed gas reservoir for potential gas leaks, the method comprising the steps of:
  providing an ultrasonic leak detector in proximity of the compressed gas reservoir, wherein the ultrasonic leak detector includes a heterodyne circuit that shifts an ultrasonic signal to an audio signal;
  detecting ultrasonic emissions from the compressed gas reservoir;
  heterodyning the ultrasonic signal to an audio signal;
  providing the audio signal to a failure condition detector that determines if the audio signal falls outside a predetermined profile;
  digitizing, by a digital audio network converter, an audio signal outside the predetermined range to a digital data stream;
  transmitting the digital data stream across a communication network to a processing unit;
  determining, by the processor, if the digital data stream represents a compressed gas leak;
  analyzing the rate-of-flow of the determined compressed gas leak;
  calculating an amount of electrical energy per unit of time needed to recharge a loss in compressed gas that results from the analyzed rate-of-flow; and
  calculating the carbon footprint created by the amount of electrical energy needed to recharge the loss in compressed gas.

20. The method of claim 19, wherein the processing unit is located remotely from the ultrasonic detector.

21. The method of claim 19, wherein the providing step includes providing a plurality of ultrasonic detectors in proximity to a plurality of respective compressed gas reservoirs.

22. The method of claim 19, further including the step of sending a control signal to a compressor coupled to the compressed gas reservoir.

23. The method of claim 19, wherein the calculation of the amount of electrical energy is based on a set of curves that show the relationship between the rate-of-flow and an amplitude of the ultrasonic emissions.

24. The method of claim 19, further including the step of displaying on a monitor connected to the processing unit the rate-of-flow of the determined gas leak.

25. The method of claim 19, further including the step of providing an estimate of cost avoidance achieved by repairing compressed gas leaks.

26. The method of claim 25, wherein the cost avoidance is measured in one of monetary and carbon footprint units.

* * * * *